(12) United States Patent
Grabenhofer et al.

(10) Patent No.: US 6,270,346 B1
(45) Date of Patent: Aug. 7, 2001

(54) DENTAL IMPLANT FOR BONE REGROWTH

(75) Inventors: Andreas Grabenhofer, Brand; Alexander Gaggl, Graz, both of (AT)

(73) Assignee: MKE Metall-und Kunststoffwaren Erzeugungs GmbH, Heidenreichstein (AT)

( * ) Notice: Subject to any disclaimer, the term of this patent is extended or adjusted under 35 U.S.C. 154(b) by 0 days.

(21) Appl. No.: 09/567,394

(22) Filed: May 9, 2000

(30) Foreign Application Priority Data

May 10, 1999 (AT) ........................................ 844/99

(51) Int. Cl.[7] .................................................. A61C 8/00
(52) U.S. Cl. ............................................................. 433/173
(58) Field of Search .................................... 433/172–176

(56) References Cited

U.S. PATENT DOCUMENTS

| 5,439,381 | * | 8/1995 | Cohen | ................................ | 433/173 |
| 5,695,335 | | 12/1997 | Haas . | | |
| 5,961,329 | | 10/1999 | Stucki-McCormick . | | |
| 6,050,819 | * | 4/2000 | Robinson | ............................ | 433/173 |

FOREIGN PATENT DOCUMENTS 96 29022    9/1996  (WO) .

* cited by examiner

*Primary Examiner*—Nicholas D. Lucchesi
(74) *Attorney, Agent, or Firm*—Herbert Dubno

(57) ABSTRACT

A dental implant has an inner root part adapted to be seated in a jawbone, an outer root part adapted to be seated in the jawbone outwardly of the inner root part, and a screw for displacing the outer root part outward relative to the inner root part. Such an implant is used by first drilling in a jawbone from an outer surface thereof a hole extending along an axis and forming in the jawbone a throughgoing first cut generally parallel to the outer surface of the jawbone and traversed by the bore. The implant member is fitted to the bore so that the inner part engages the jawbone to one side of the cut and the outer part engages the jawbone to the other side of the cut. Then the jawbone is cut again generally parallel to the first cut is free from the jawbone a piece of bone engaged by the outer part. Subsequently the core-member parts are periodically axially separated by means of the screw to axially outwardly displace the piece of bone from the jawbone and promote bone growth in the cut until the piece of bone has been moved axially outward a predetermined distance from the jawbone. Finally a dental prosthesis is mounted on an outer end of the outer part.

14 Claims, 5 Drawing Sheets

DENTAL IMPLANT FOR BONE REGROWTH

SPECIFICATION

1. Field of the Invention

The present invention relates to a dental implant. In addition this invention concerns a method of promoting bone regrowth while doing a dental implant.

2. Background of the Invention

A standard dental implant comprises an endosseous root member that is set in the upper or lower jaw, a coronal or head part that is fixed to the root member, and the actual dental prosthetic that is mounted on the head part. Normally the gum or mucosa is cut to reveal the jaw bone and a hole is drilled in the living bone. Then the root member is fitted, normally screwed, into the hole, and is provided with a transmucosal cap dimensioned to project through the gum. Then the incision is sutured up and the site is allowed to heal, with the root member becoming integrated into the jaw bone and the gum healing neatly around the cap. The cap is then normally unscrewed from the root and replaced with a head part or mount of similar dimensions to which the actual prosthesis is mounted.

A significant problem is that typically the implant is needed in a location where a tooth has been missing for quite some time. As a result of the lack of a tooth at this side, the jaw bone has not received the necessary mechanical stimulation to ensure its good health, so it has atrophied and shrunk. Thus the implant must be installed just at a particularly weak point.

OBJECTS OF THE INVENTION

It is therefore an object of the present invention to provide an improved dental implant.

Another object is the provision of such an improved dental implant which overcomes the above-given disadvantages, that is which encourages bone regrowth.

A further object is to provide a method of encouraging bone regrowth at the site of a dental implant.

SUMMARY OF THE INVENTION

A dental implant has according to the invention an inner root part adapted to be seated in a jawbone, an outer root part adapted to be seated in the jawbone outwardly of the inner root part, and a screw for displacing the outer root part outward relative to the inner root part.

Such an implant is used by first drilling in a jawbone from an outer surface thereof a hole extending along an axis and forming in the jawbone a throughgoing first cut generally parallel to the outer surface of the jawbone and traversed by the bore. The implant member is fitted to the bore so that the inner part engages the jawbone to one side of the cut and the outer part engages the jawbone to the other side of the cut. Then the jawbone is cut again generally parallel to the first cut to free from the jawbone a piece of bone engaged by the outer part. Subsequently the core-member parts are periodically axially separated to axially outwardly displace the piece of bone from the jawbone and promote bone growth in the cut until the piece of bone has been moved axially outwardly a predetermined distance from the jawbone. Finally a dental prosthesis is mounted on an outer end of the outer part.

This system makes it possible to promote bone regrowth in the manner used, for instance on serious long-bone fractures. It is known that when for example, a femur is broken with bone loss that the two parts can be periodically pulled apart at the fracture site until the bone has the desired length, the regrown bone filling the gap created as the bone parts are distracted. In this manner a seriously shrunken and atrophied jaw bone can be rebuilt so that it will provide solid support for the dental prosthesis by means of the implant.

According to the invention the root parts have outer surfaces each formed with a screwthread. The screwthread of the inner root part is deeper than the screwthread of the outer root part so that it can better engage in the spongier bone it will be set in. It is possible to eliminate the screwthread on the inner part since it is only subjected to compression when in use.

The parts are provided with axially interengaging formations rotationally coupling the parts together and the outer part is formed with tool-engaging facets. Thus the two-part core member can be screwed into the bore formed in the jaw in the standard manner, care being taken that the outer part only engages the jawbone outward of the cut and the inner part inward thereof. The inner part is internally threaded and engages the screw and the screw has a head bearing axially in both directions on the outer part. Furthermore the outer part includes a retaining nut formed with a central axial passage and bearing axially inward on the screw head and the inner part has an extension tube axially slidable in the outer part. The coupling formations need only be effective when the core member is being screwed in; once installed it is no longer necessary so that it is irrelevant if these formations are pulled apart and rendered ineffective.

To solidly fix the piece of bone to the outer core part a ring is releasably engaged with an inner end of the outer part. This ring bears against the inner face of the piece of bone so that as the outer part is moved axially out, it bears via this ring, which can be set in a groove of the outer part, on the piece of bone. The ring can be provided with a set screw bearing on the outer part and can have a large diameter central hole so it can tip relative to the outer part. In this system the inner end is inwardly flared. Normally the piece of bone is initially separated completely or widely enough by means of the outer part to allow a special instrument to install the ring on the inner end of the outer part, then the parts are reassembled and the piece fitted back relatively tightly in the pocket formed in the jawbone. The ring later assists pulling out the piece, which will adhere fairly strongly as bone regrows so that the extra force needed can be applied via the ring and not solely through the screwthreads of the outer part.

The implant has according to the invention can include a mounting head having an inner face engaging an outer face of the outer face and secured thereto by the screw. These faces can have complementary interengaging frustoconical surfaces to prevent tissue from growing inside the implant. Alternately one of the faces is planar and the other of the faces is flared and has an edge engaging the one face in line contact.

To stiffen the core member, the mounting head has a tubular extension engaging into the outer part.

According to the invention the dental prosthesis is mounted by removing the screw from the core member, mounting a head part on an outer face of the core member, securing the head part to the core member by means of another screw, and installing the prosthesis on the head part. Thus a transmucosal collar that is used while the gums heal and as core-member parts are being distracted to promote bone growth is replaced with a standardized head part whose axial dimension is determined by the thickness of the gum tissue, the depth of the core member, and the type of implant, is mounted on the outer part for securing to it of the dental prosthesis.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
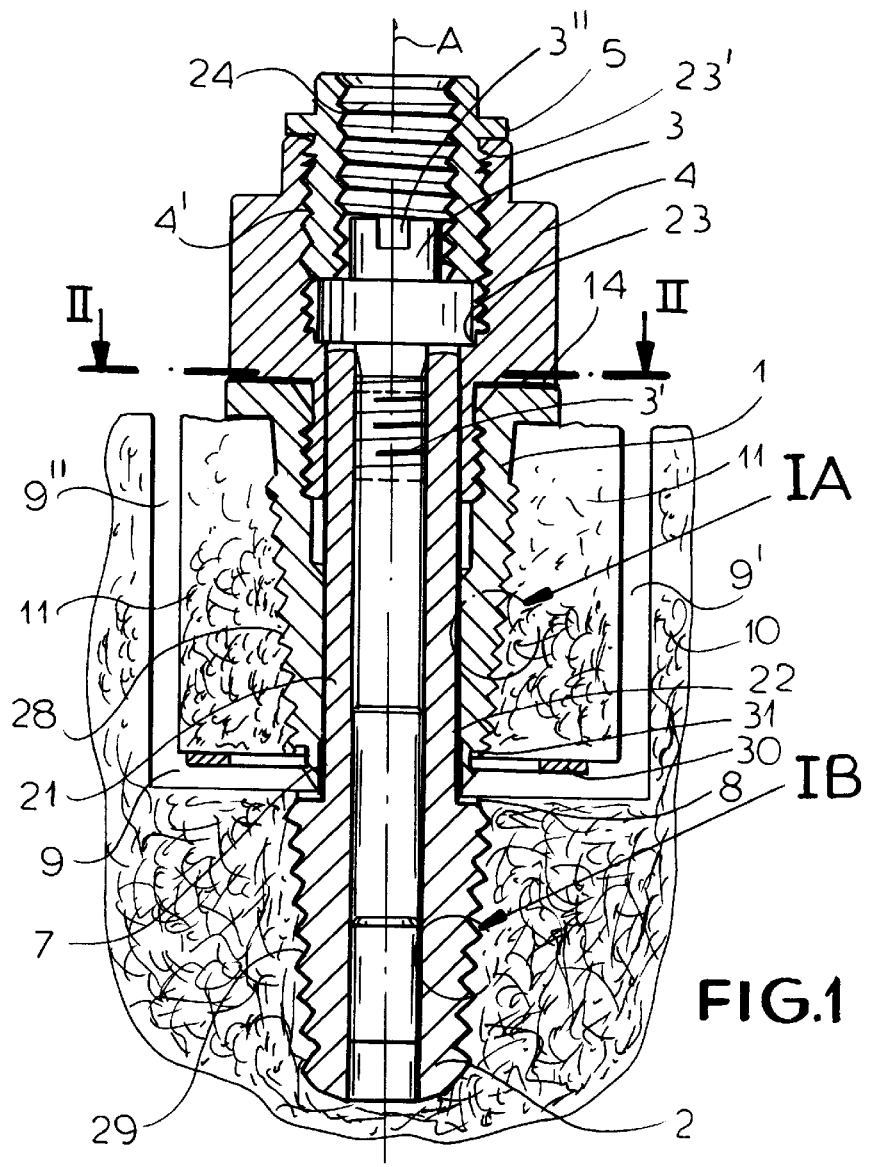
FIG. 1 is a section through an implant according to the invention in a starting position.
Figure 1A:
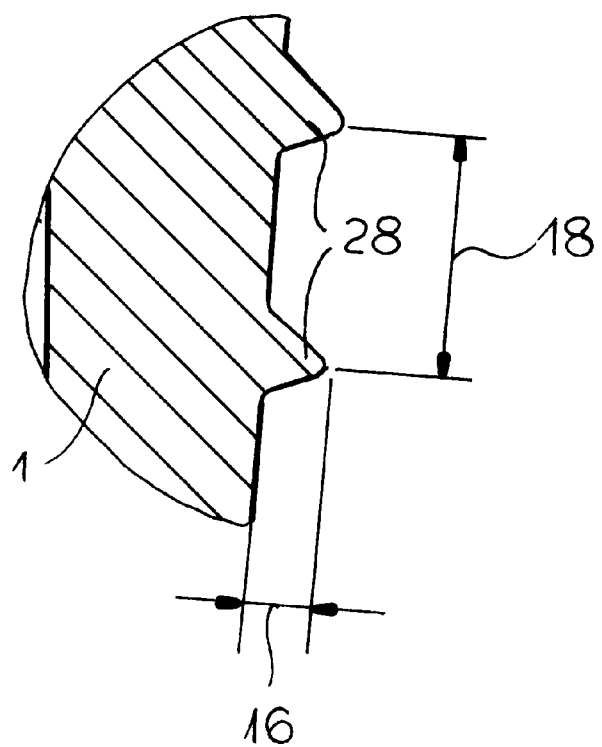
FIGS. 1A and 1B are large-scale views of the details indicated at IA and IB in FIG. 1.
Figure 1B:
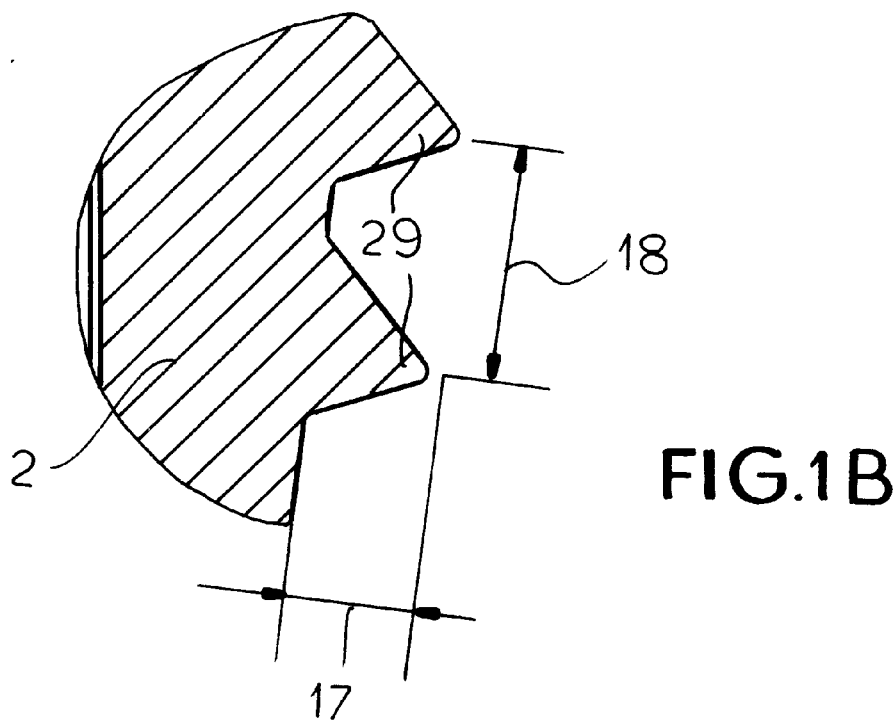

As seen in FIG. 1 a dental implant according to the invention has an outer root part 1 and an inner root part 2 both centered on a common axis A and seated in a jawbone 10. The parts 1 and 2 have frustoconical outer surfaces and are formed with screwthreads 28 and 29 of identical pitch 18, but the screwthread 28 has a thread depth 16 (FIG. 1A) that is substantially less than the depth 17 of the threads 29, since the inner part 2 is normally seated in somewhat spongier bone.

Figure 2:
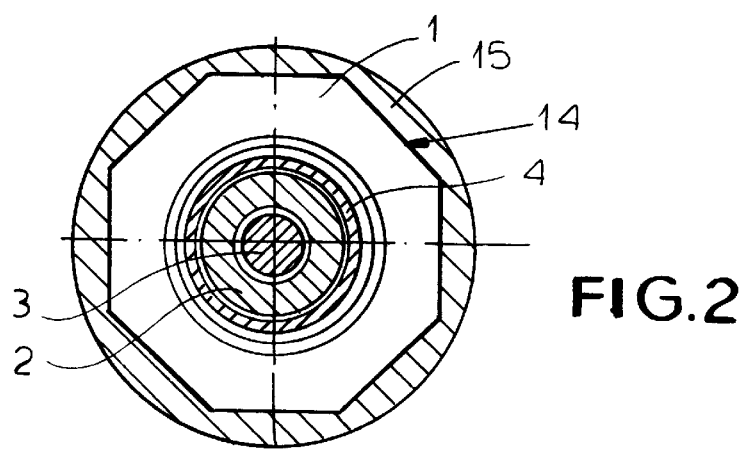
FIG. 2 is a section taken along line II—II of FIG. 1.

The inner part 2 is formed with an axially outwardly extending and internally threaded tube 21 coaxially received in a bore 22 of the outer part 1 and formed with an internal screwthread. The inner end of the outer part 1 is formed with axially inwardly extending projections 7 that engage in axially outwardly open grooves or seats 8 of the inner part 2 so that, when the projections 7 engage in the grooves 8, the two parts 1 and 2 are rotationally coupled to each other. In addition the inner end of the outer part 1 is formed with a radially outwardly open groove 31 to which is fitted a slotted ring 30 whose function is described in more detail below. The upper end of the outer part 1 is formed with facets 14 adapted to fit with a tool such as the socket wrench shown at 15 in FIG. 2.

A transmucosal sleeve 4 is formed with an internal screwthread 4' and with a planar face 4" that sits flatly on the outer face of the outer part 1. A screw 3 has a threaded shank 3' engaged in the internally threaded tube 21 and a head that bears axially forward on a shoulder 23 of the sleeve 4 and axially backward on a tubular retaining nut 5 threaded into the screwthread 4'. The nut 5 is formed with an axially throughgoing passage 24 giving access to a tool socket 3" at the outer end of the screw 3.

As illustrated in FIG. 1 the above-described parts are adapted to be mounted in the jawbone 10 which has been cut horizontally at 9. A tapered hole is drilled in the jawbone 10, the outer part 1 is fitted to the wrench 15 and it is screwed into the living bone. The cut 9 is at such a depth below the surface that it will be level with the groove 31. Once the parts 1 and 2 are in place, the ring 30 is slid in from the side to fit with the groove 31 and further cuts 9' and 9" are formed parallel to the axis down to the horizontal cut 9 to free a piece 11 of bone from the jawbone 10.

Once this is done the screw 3 can be rotated to move the two parts 1 and 2 axially apart, increasing the gap at the cut 9. This will cause new bone to regrow in this location. Normally the parts 1 and 2 are spread axially at a rate from 0.1 mm to 1.0 mm per day, depending on the rate of bone regrowth, until the desired amount of regrowth has been achieved.

Figure 3:
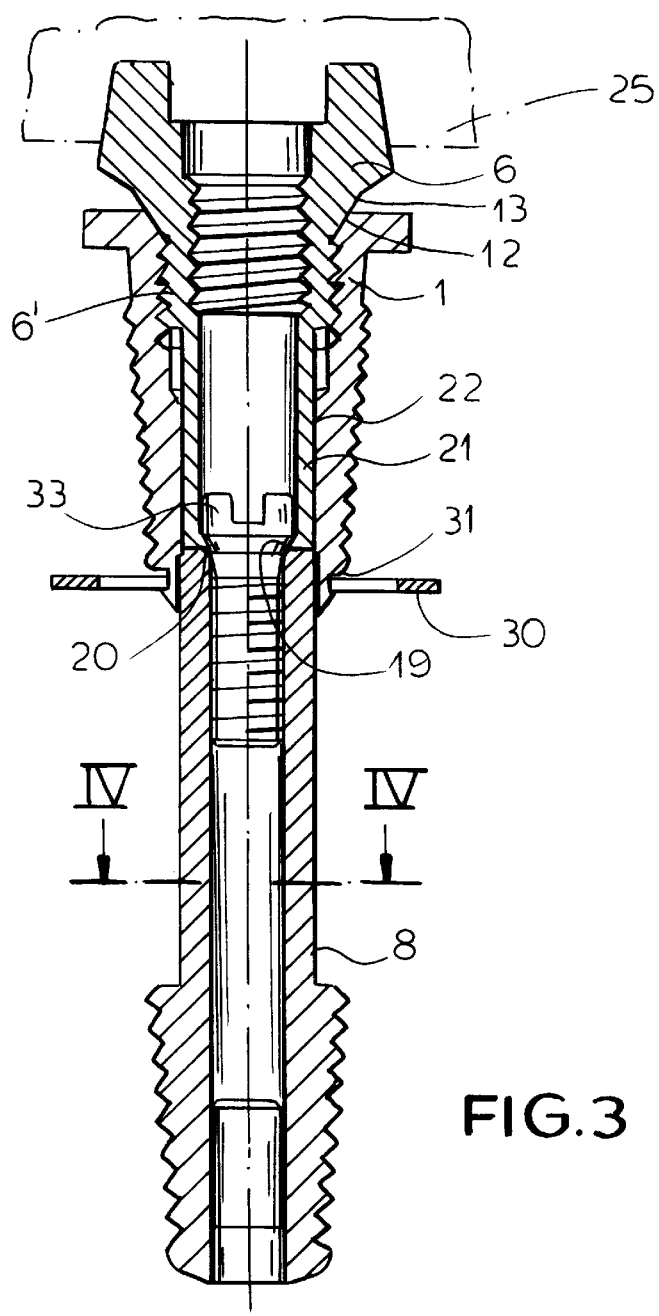
FIG. 3 is a view like FIG. 1 but with the implant in a final position.
Figure 4:
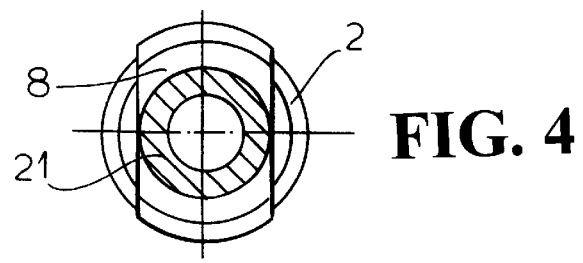
FIG. 4 is a section taken along line IV—IV of FIG. 3.

This can be continued until the two parts 1 and 2 are in the relative positions shown in FIG. 3. At this time the screw 3 is screwed completely back out to remove the transmucosal sleeve 4, the nut 5, and the screw 3, and these part are replaced by a coronal mounting part 6 that has a frustoconical surface 13 fitting with a frustoconical surface 12 of the outer part 1 and an inner end formed with another frustoconical surface 19 engaging a frustoconical surface 20 of a screw 33 threaded into the part 1 and replacing the screw 3. The part 6 provides the mount for a prosthesis illustrated schematically at 25, which can be a bridge, single tooth, or the like.

Figure 5:
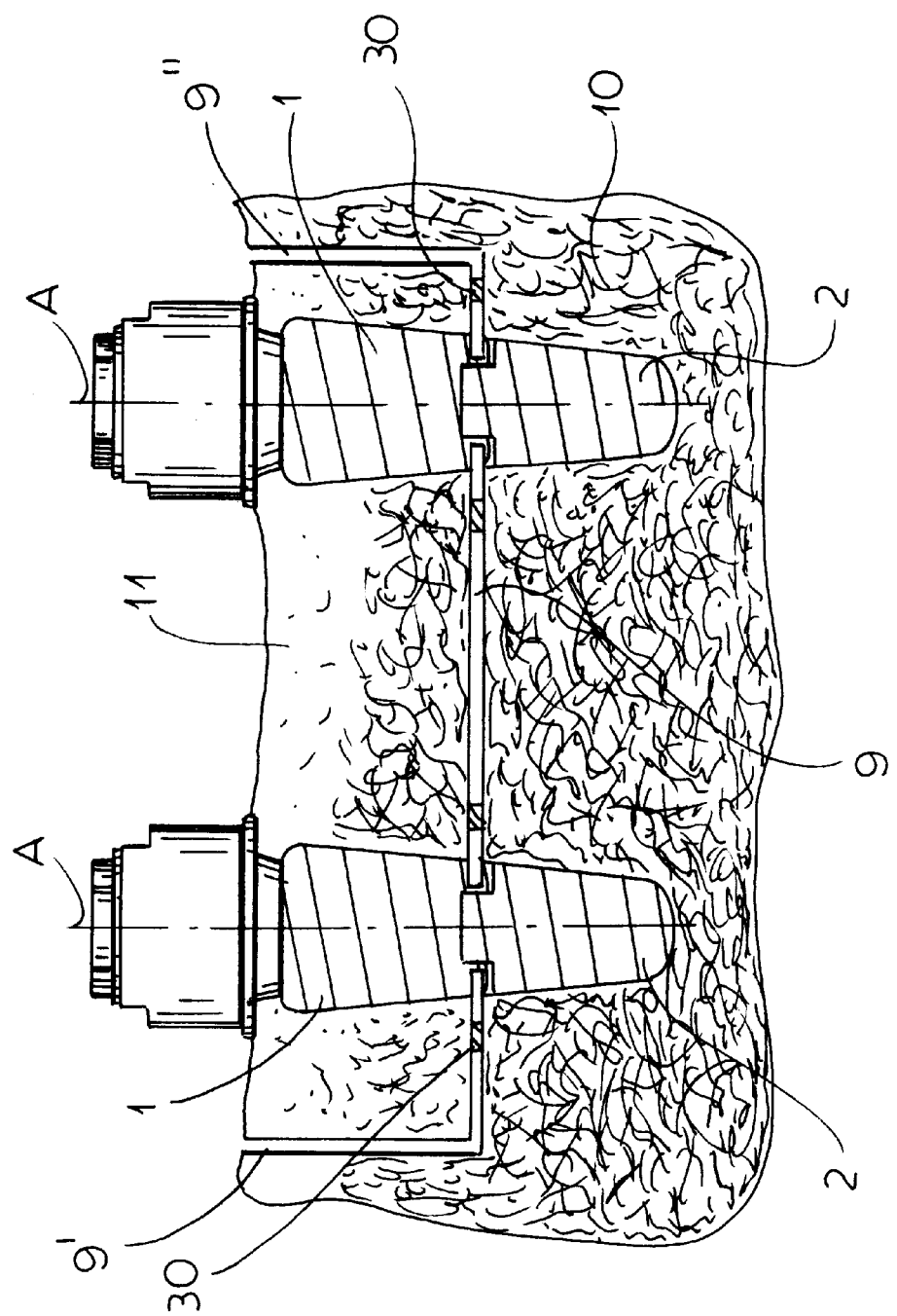
FIG. 5 is a section through a jawbone showing the use of a pair of the implants in accordance with the invention.

FIG. 5 show how two such implants 1, 2 with their axes A parallel can be set in the jawbone 10 to lift a fairly large plug 11. Such a system can be used where substantial bone regrowth over a relatively long area is needed.

Figure 6:
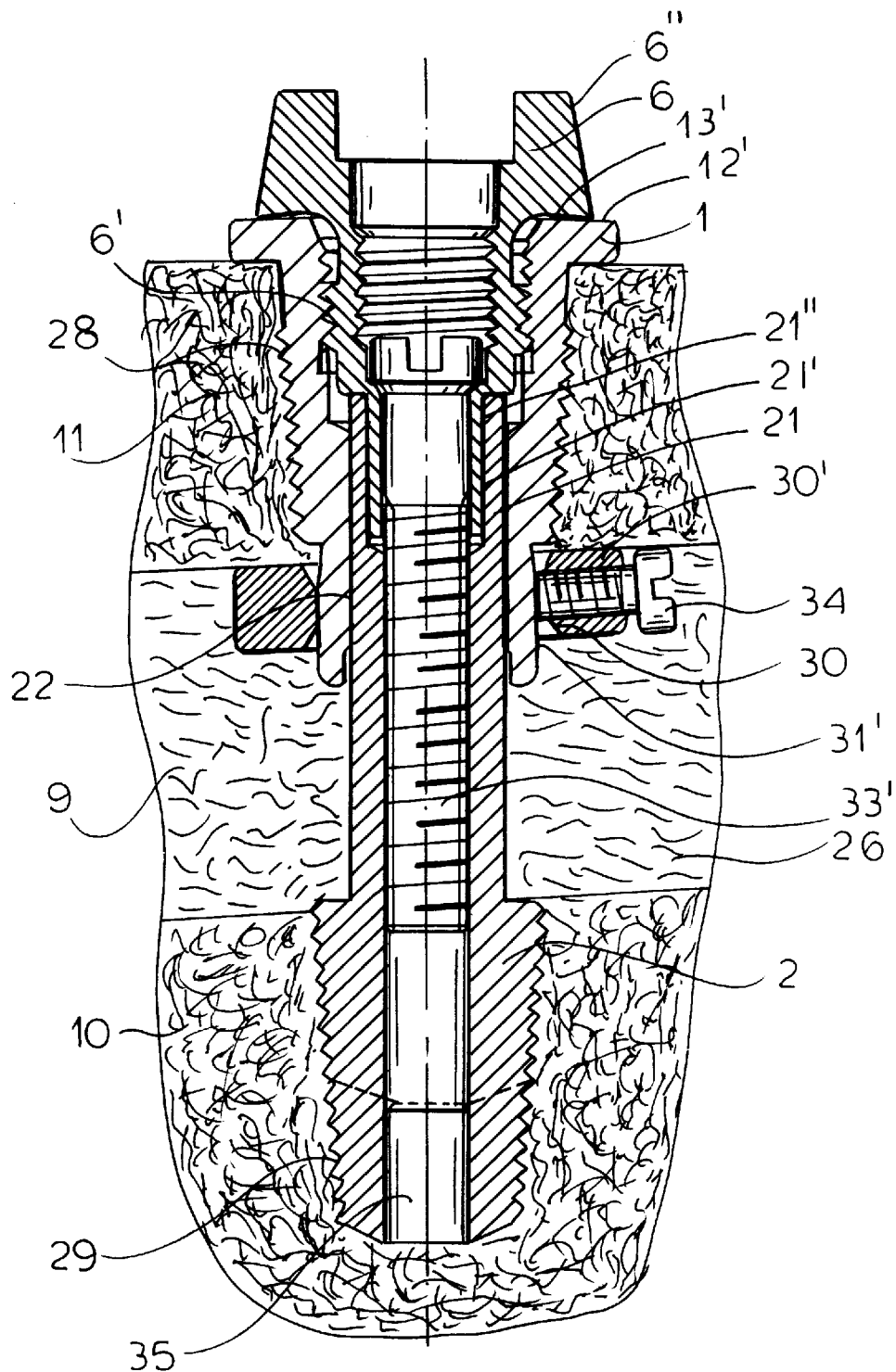
FIG. 6 is a view like FIG. 3 of another installed implant according to the invention in the final position.

In FIG. 6 a finished implant is shown with the cut 9 filled with regrown bone 26. Here the slot 31 is eliminated and instead the inner end of the outer part 1 has a frustoconically inwardly flared inner surface 31' on which the ring 30' is secured by a set screw 34. This ring 30' has a double outwardly flared center hole 30" so it can be mounted at an angle to flatly engage the outer face of the cut 9. In addition here the coronal part 6 has a frustoconical lower surface 13" that flares downward to sit with a sharp edge on a planar end face 12' of the part 1. The part 6 further has an axially extending portion 21' received coaxially in an extension 21" of the tube 21 and a fairly long screw 33' extends from the part 6 all the way down into the outer region of the part 2, greatly reinforcing the structure. A plug 35 blocks the outer end of the tubular part 2.

We claim:

1. A dental implant comprising:
an internally threaded inner root part centered on an axis, adapted to be seated in a jawbone, and formed with an extension tube extending axially outward;
an outer root part adapted to be seated in the jawbone outwardly of the inner root part and axially slidable on the extension tube; and
means including a screw threaded into the inner part and having a head bearing axially in both directions on the outer part for displacing the outer root part outward relative to the inner root part and sliding the outer part on the extension tube of the inner part.

2. The implant defined in claim 1 wherein the root parts have outer surfaces each formed with a screwthread.

3. The implant defined in claim 2 wherein the screwthread of the inner root part is deeper than the screwthread of the outer root part.

4. The implant defined in claim 1 wherein the parts are provided with axially interengaging formations rotationally coupling the parts together.

5. The implant defined in claim 4 wherein the outer part is formed with tool-engaging facets.

6. The implant defined in claim 1 wherein the outer part includes a retaining nut formed with a central axial passage and bearing axially inward on the screw head.

7. The implant defined in claim 1, further comprising
a ring releasably engaged with an inner end of the outer part.

8. The implant defined in claim 7 wherein the ring is provided with a set screw bearing on the outer part.

9. The implant defined in claim 7 wherein the ring has a large diameter central hole so it can tip relative to the outer part.

10. The implant defined in claim 7 wherein the inner end is inwardly flared.

11. The implant defined in claim 1, further comprising
a mounting head having an inner face engaging an outer face of the outer part and secured thereto by the screw.

12. The implant defined in claim 11 wherein the faces have complementary interengaging frustoconical surfaces.

13. The implant defined in claim 11 wherein one of the faces is planar and the other of the faces is flared and has an edge engaging the one face in line contact.

14. The implant defined in claim 11 wherein the mounting head has a tubular extension engaging into the outer part, the screw extending from the outer part through the extension to an inner end of the inner part.

* * * * *